(12) United States Patent
Kawashima

(10) Patent No.: US 7,582,473 B2
(45) Date of Patent: Sep. 1, 2009

(54) APPARATUS AND METHOD FOR ANALYZING BACTERIA

(75) Inventor: Yasuyuki Kawashima, Kobe (JP)

(73) Assignee: Sysmex Corporation, Hyogo (JP)

( * ) Notice: Subject to any disclaimer, the term of this patent is extended or adjusted under 35 U.S.C. 154(b) by 284 days.

(21) Appl. No.: 10/922,522

(22) Filed: Aug. 19, 2004

(65) Prior Publication Data

US 2005/0042744 A1    Feb. 24, 2005

(30) Foreign Application Priority Data

Aug. 22, 2003    (JP)    ............... 2003-299208

(51) Int. Cl.
  *C12M 1/34*    (2006.01)
  *C12M 3/00*    (2006.01)
  *G01N 21/00*   (2006.01)
  *G01J 3/44*    (2006.01)
  *G01N 15/02*   (2006.01)

(52) U.S. Cl. ............... 435/288.7; 435/808; 435/288.3; 435/288.4; 435/288.5; 378/44; 378/70; 378/86; 422/82.08; 250/483.1; 250/574; 356/73; 356/301; 356/336; 356/337

(58) Field of Classification Search ............. 435/288.7, 435/808, 288.4, 288.5, 288.3; 378/44, 86, 378/70; 422/82.08; 250/483.1, 574; 356/73, 356/301, 336, 337
See application file for complete search history.

(56) References Cited

U.S. PATENT DOCUMENTS

| | | | |
|---|---|---|---|
| 5,236,827 A | | 8/1993 | Sussman et al. |
| 5,308,772 A | * | 5/1994 | Sakata et al. .................. 436/63 |
| 5,939,326 A | * | 8/1999 | Chupp et al. .................. 436/43 |
| 6,567,678 B1 | * | 5/2003 | Oosta et al. ................ 600/316 |
| 6,677,132 B1 | | 1/2004 | Hofler et al. |
| 2002/0006631 A1 | * | 1/2002 | Houwen et al. ............ 435/7.24 |
| 2002/0148729 A1 | | 10/2002 | Armstrong |
| 2006/0147978 A1 | * | 7/2006 | Lorens et al. .................. 435/6 |

FOREIGN PATENT DOCUMENTS

| | | |
|---|---|---|
| EP | 0 818 540 A1 | 1/1998 |
| EP | 1 136 563 A2 | 9/2001 |
| EP | 1 203 825 A2 | 5/2002 |
| WO | WO 00/70078 | 11/2000 |

* cited by examiner

*Primary Examiner*—William H Beisner
*Assistant Examiner*—Nathan A Bowers
(74) *Attorney, Agent, or Firm*—Brinks Hofer Gilson & Lione

(57) ABSTRACT

An apparatus for analyzing bacteria is described that includes an analyte sample preparing section for preparing an analyte sample from a specimen; a detector for detecting optical information from each particle in the analyte sample; and a controller for detecting non-fermentative bacteria on the basis of the detected optical information. A method for analyzing bacteria is also described.

16 Claims, 9 Drawing Sheets

APPARATUS AND METHOD FOR ANALYZING BACTERIA

This application claims priority under 35 U.S.C. § 119 to Japanese Patent Application No. 2003-299208 filed Aug. 22, 2003, the entire content of which is hereby incorporated by reference.

BACKGROUND

1. Field of the Invention

The present invention relates to a method and an apparatus for detecting non-fermentative bacteria contained in a specimen. Also, the present invention relates to a method and an apparatus for detecting fermentative bacteria and non-fermentative bacteria contained in a specimen. Also, the present invention relates to a method and an apparatus for determining whether the kind of the bacteria contained in a specimen is fermentative bacteria or non-fermentative bacteria. Also, the present invention relates to a method and an apparatus for determining whether the principal bacteria contained in a specimen are fermentative bacteria or non-fermentative bacteria.

2. Description of the Related Art

Bacteria are classified into fermentative bacteria that produce an acidic final product by decomposing sugar and non-fermentative bacteria incapable of decomposing sugar.

As a method for detecting fermentative bacteria, one can mention a Methyl Red reaction test.

When bacteria decompose sugar contained in a medium, an acidic product is produced. In the Methyl Red reaction test, a Methyl Red reagent is used as a pH indicator, whereby the acidification of the medium (i.e. lowering of the pH of the medium) is detected by a change in the color of the added pH indicator. By this change in the color of the medium, one can find whether the sugar in the medium has been decomposed or not, whereby one can detect fermentative bacteria. Generally, in classifying bacteria into fermentative bacteria and non-fermentative bacteria, the Methyl Red reaction test is carried out using a medium that contains purely cultivated bacteria. Then, the bacteria are classified into fermentative bacteria and non-fermentative bacteria on the basis of whether fermentative bacteria have been detected or not.

However, the above-mentioned method requires cultivation for examining whether the bacteria decompose sugar or not, so that it requires about two to three days before fermentative bacteria are detected. Thus, the conventional method requires cultivation work to detect fermentative bacteria. Such cultivation work is cumbersome and requires a long period of time.

As a technique for automatically analyzing bacteria without being accompanied by cultivation of the bacteria, a method disclosed in European Patent Publication No. 1136563 is known. According to this method, by allowing a cationic surfactant to act on a sample containing bacteria, the dye transmittance of the bacteria is promoted. By this, the stainability of the bacteria is enhanced. Then, by performing a fluorescence staining treatment and detecting the fluorescence emitted by the bacteria with a flow cytometer, the bacteria in the sample are detected. With the use of a technique such as described above, one can automatically detect bacteria in a specimen in a comparatively short period of time. However, using such a method, one cannot detect bacteria in a specimen by further classifying the bacteria into fermentative bacteria and non-fermentative bacteria.

BRIEF SUMMARY

The present invention provides a method and an apparatus for detecting non-fermentative bacteria more simply and rapidly than the conventional techniques.

Also, the present invention provides a method and an apparatus for detecting fermentative bacteria and non-fermentative bacteria more simply and rapidly than the conventional techniques.

Also, the present invention provides a method and an apparatus for determining whether the kind of the bacteria contained in a specimen is fermentative bacteria or non-fermentative bacteria more simply and rapidly than the conventional techniques.

Also, the present invention provides a method and an apparatus for determining whether the principal bacteria contained in a specimen are fermentative bacteria or non-fermentative bacteria more simply and rapidly than the conventional techniques.

DETAILED DESCRIPTION OF THE DRAWINGS AND THE PRESENTLY PREFERRED EMBODIMENTS

Hereafter, a bacteria analyzing apparatus according to an embodiment of the present invention will be described.

Figure 1:
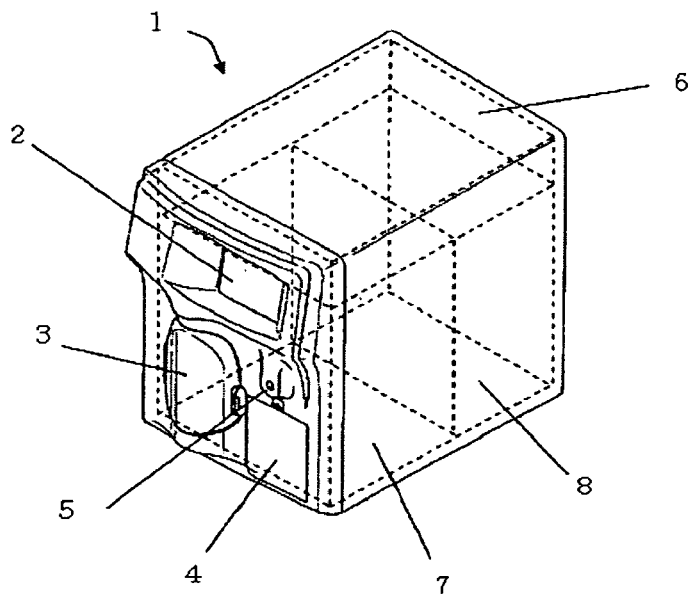
FIG. 1 is a view describing a construction of a bacteria analyzing apparatus according to one embodiment of the present invention.

FIG. 1 is a view illustrating a bacteria analyzing apparatus 1 in which the outer appearance of the apparatus is shown in solid lines, and the schematic construction of the inside of the apparatus is shown in broken lines. A liquid crystal touch panel 2 for performing various setting inputs and displaying and outputting the measurement results, a specimen setting section cover 3, a reagent setting section cover 4, and a start switch 5 are disposed on the front surface of bacteria analyzing apparatus 1. Further, a controlling section 6 that controls the operation of the apparatus and the analyzing process is disposed at the top of the inside of bacteria analyzing apparatus 1 shown in broken lines. An analyte sample preparing section 7 for preparing a sample liquid is disposed on the front side of the lower part. A measuring section 8 for detecting a signal from the sample liquid is disposed on the backside of the lower part.

Figure 2:
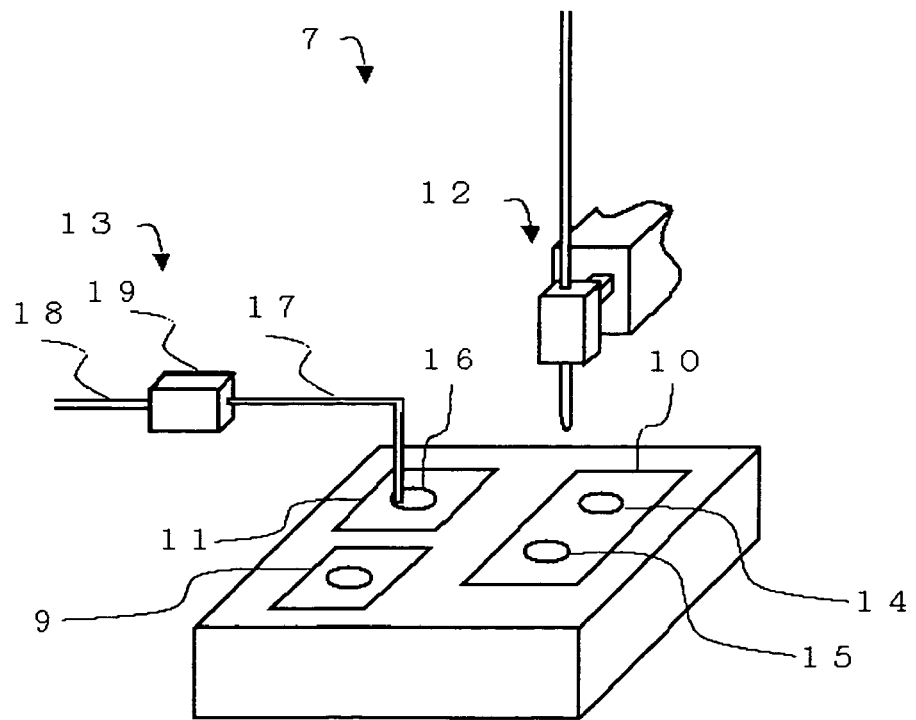
FIG. 2 is a view describing an analyte sample preparing section of the bacteria analyzing apparatus according to one embodiment of the present invention.

FIG. 2 is a view illustrating analyte sample preparing section 7. Analyte sample preparing section 7 is made of a specimen setting section 9, a reagent setting section 10, a staining section 11, a dispensing device 12, and a liquid transporting device 13. An operator opens the aforementioned specimen setting section cover 3 of FIG. 1 to set a specimen container containing a specimen into specimen setting section 9. Also, the operator opens reagent setting section cover 4 of FIG. 1 to set a micro test tube 14 containing a staining liquid and a micro test tube 15 containing a diluting liquid respectively into a reagent setting section 10. A micro test tube 16 is set in staining section 11. Further, the specimen is mixed with the staining liquid and the diluting liquid in micro test tube 16 for preparation of an analyte sample. Here, though not illustrated in the drawings, staining section 11 is provided with a temperature regulating mechanism for maintaining the solution in micro test tube 16 at a constant temperature and a stirring mechanism for stirring the solution in micro test tube 16. A dispensing device 12 is adapted to suck and eject a predetermined amount of liquid through the tip end thereof, and also dispensing device 12 is adapted to be movable upwards, downwards, rightwards, leftwards, frontwards, and rearwards by a driving device (not illustrated). Liquid transporting device 13 is composed of a suction tube 17 for sucking an analyte sample, a liquid transporting pipe 18 for transporting the analyte sample sucked from suction tube 17 to measuring section 8 illustrated in FIG. 3, and a pump 19 for sucking the analyte sample and transporting the analyte sample to measuring section 8. Suction tube 17 is inserted into micro test tube 16 set in staining section 11 so as to suck a predetermined amount of the analyte sample. The sucked analyte sample is transported to measuring section 8 through liquid transporting pipe 18.

Figure 3:
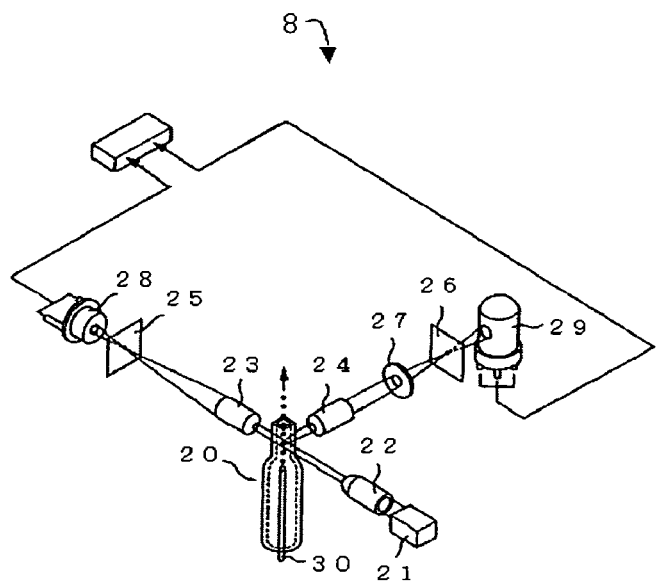
FIG. 3 is a view describing a measuring section of the bacteria analyzing apparatus according to one embodiment of the present invention.

FIG. 3 is a view describing measuring section 8. Measuring section 8 is provided with a sheath flow cell 20, a laser light source 21, a condenser lens 22, converging lenses 23, 24, pin holes 25, 26, a filter 27, a photodiode 28, and a photomultiplier tube 29. Sheath flow cell 20 is for allowing the analyte sample prepared in the aforementioned analyte sample preparing section 7 of FIG. 2 to flow therethrough. Also, referring to FIG. 4, sheath flow cell 20 is provided with a sample nozzle 30 for jetting the analyte sample liquid upwards towards a narrow through-hole section 33, a sheath liquid supplying inlet 31, and an exhaust liquid outlet 32. Converging lenses 23, 24 collect optical information such as a forward scattered light or side fluorescent light obtained from each particle in the sample that has received a laser beam. Photodiode 28 receives and performs photoelectric conversion on the forward scattered light to output an electric signal. Photomultiplier tube 29 receives and performs photoelectric conversion on the side fluorescent light to output an electric signal. The output signals are each sent to controlling section 6.

Figure 5:
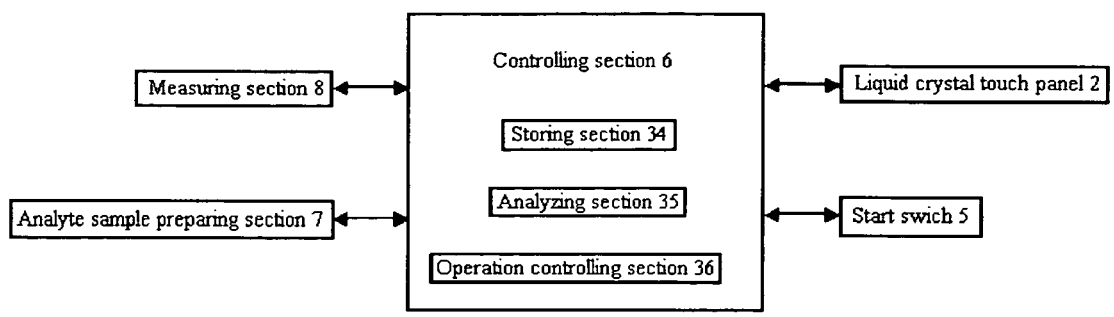
FIG. 5 is a view describing a relationship between a controlling section of the bacteria analyzing apparatus and each section of the apparatus according to one embodiment of the present invention.

FIG. 5 is a view illustrating a construction of controlling section 6 and a relationship between controlling section 6 and each section of the apparatus. Controlling section 6 includes a microcomputer having a central processing unit (CPU) and a storage device such as a ROM or RAM and a circuit for processing the signals sent from measuring section 8. Controlling section 6 functions as a storage section 34, an analyzing section 35, and an operation controlling section 36. Storage section 34 stores analyzing programs for analyzing the signals obtained from particles in the sample and controlling programs for controlling the operation of each section in the apparatus. Further, storage section 34 stores data of the signals detected by measuring section 8 and the results of processing by the analyzing programs. Analyzing section 35 analyzes the signals detected by measuring section 8 in accordance with the analyzing programs and creates data related to the bacteria contained in the analyte sample liquid. The data created in analyzing section 35 are output to liquid crystal touch panel 2. Operation controlling section 36 controls the operation of each section in the apparatus in accordance with the controlling programs stored in storage section 34.

Hereafter, the operation of the apparatus will be described in detail.

First, an operator sets a specimen and reagents for measurement to predetermined positions in analyte sample preparing section 7. The specimen can be set into specimen setting section 9 of the aforementioned analyte sample preparing section 7 of FIG. 2 by opening the aforementioned specimen setting section cover 3 of FIG. 1. Further, regarding the reagents such as a staining liquid and a diluting liquid, micro test tube 14 containing the staining liquid and micro test tube 15 containing the diluting liquid can be each set into reagent setting section 10 of analyte sample preparing section 7 by opening reagent setting section cover 4.

Liquid containing bacteria is used as the specimen. For example, a bacteria liquid obtained by collecting a colony of bacteria and suspending the bacteria into liquid, urine or blood containing bacteria, or the like can be used as the specimen.

The staining liquid contains a polymethine type fluorescent dye represented by the following structural formula. This dye has a property of being specifically bonded to a nucleic acid of bacteria, so that a staining liquid containing this dye can specifically stain the bacteria.

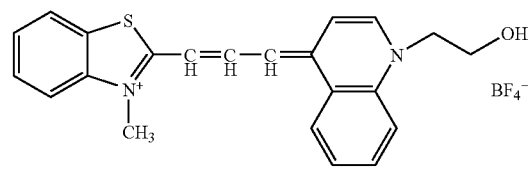

The diluting liquid may have the following composition.

| Reagent composition (diluting liquid) | |
|---|---|
| Citric acid | 100 mM |
| Sodium sulfate | 90 mM |
| Amidosulfuric acid | 100 mM |
| NaOH amount giving pH 1.5 | |

Figure 6:
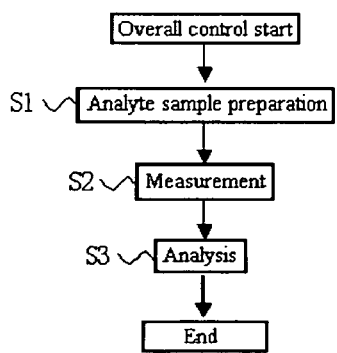
FIG. 6 is a view describing a flow of the overall control of the bacteria analyzing apparatus according to one embodiment of the present invention.

When the specimen and the reagents are set in this manner and a start switch 5 is pressed, an overall control is started. FIG. 6 is a flowchart showing the flow of the overall control by the controlling programs. When the start switch is pressed, the steps S1 (analyte sample preparation), S2 (measurement), and S3 (analysis) are successively executed. Analyte sample preparing section 7, measuring section 8, and analyzing section 35 are controlled by the controlling programs, whereby a series of operations are automatically carried out. The above-mentioned steps S1, S2, and S3 will be described below.

S1 (Analyte Sample Preparation)

An operation of analyte sample preparing section 7 in analyte sample preparation will be described with reference to FIG. 2. First, dispensing device 12 sucks a specimen from a specimen container set in specimen setting section 9, and dispenses 50 μL into micro test tube 16 set in staining section 11. Next, dispensing device 12 sucks a diluting liquid from micro test tube 15 set in reagent setting section 10, and dispenses 340 μL into micro test tube 16 set in staining section 11. Further, dispensing device 12 sucks a staining liquid from micro test tube 14 set in reagent setting section 10, and dispenses 10 μL into micro test tube 16 set in staining section 11. Thereafter, staining section 11 stirs the mixture for 30 seconds while maintaining micro test tube 16 at a temperature of 42° C. This prepares an analyte sample in micro test tube 16.

In the above-described preparation of an analyte sample, the specimen is processed under an acidic condition by using an acidic diluting liquid, and the bacteria in the specimen are stained. Fermentative bacteria produce an acidic product in decomposing sugar, as described in the Description of the Related Art. For this reason, fermentative bacteria can survive even under an acidic condition in which bacteria usually find difficult to live. On the other hand, non-fermentative bacteria die or suffer from damage of their cell membranes or cell walls under an acidic condition. Therefore, when a specimen is treated under an acidic condition, non-fermentative bacteria suffer from damage of their cell membranes or cell walls, so as to promote dye transmittance. This lets the substances in the cells of the non-fermentative bacteria be efficiently bonded to dyes. As a result of this, non-fermentative bacteria will have a higher degree of stainability than fermentative bacteria. In this embodiment, fluorescent staining is carried out, so that, by detecting fluorescence from each bacterium in the specimen, fermentative bacteria and non-fermentative bacteria can be easily distinguished by the difference of fluorescence intensity. In other words, the fluorescence intensity obtained from non-fermentative bacteria is higher than the fluorescence intensity obtained from fermentative bacteria. Here, the acidic condition shown above is preferably pH 1.0 to 3.0, most preferably 1.0 to 2.0.

When the analyte sample is prepared, the analyte sample is sucked from micro test tube 16 of staining section 11 by liquid transporting device 13, and is sent to sheath flow cell 20 of measuring section 8.

S2 (Measurement)

Figure 4:
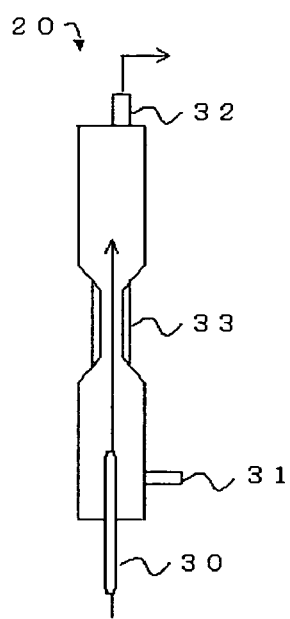
FIG. 4 is a view describing a sheath flow cell part of the bacteria analyzing apparatus according to one embodiment of the present invention.

An operation of measuring section 8 in the measurement will be described with reference to FIGS. 3 and 4. The analyte sample prepared in analyte sample preparing section 7 is guided to sheath flow cell 20, and the sample liquid is ejected into the sheath flow cell through sample nozzle 30. Simultaneously with this, a sheath liquid is ejected into the sheath flow cell through sheath liquid supplying inlet 31. By this, the sample liquid is surrounded by the sheath liquid within the sheath flow cell, and is further narrowed down by narrow through-hole section 33 to flow. By narrowing the flow of the sample liquid to the same degree as the particle size, the particles contained in the sample liquid are arranged in one line to flow through the narrow through-hole section.

A laser beam emitted from laser light source 21 is narrowed by condenser lens 22 and is radiated onto the sample stream flowing through narrow through-hole section 33. The forward scattered light emitted from each particle in the sample that has received the laser beam is converged by converging lens 23 to pass through pin hole 25. The side fluorescent light is converged by converging lens 24 to pass through filter 27 and pin hole 26. Then, the forward scattered light is received and undergoes photoelectric conversion by photodiode 28, and the side fluorescent light is received and undergoes photoelectric conversion by photomultiplier tube 29, and are output respectively as a forward scattered light signal and a side fluorescent light signal. Each signal is sent to controlling section 6, and is stored into storage section 34 as data of individual particles.

S3 (Analysis)

Figure 7:
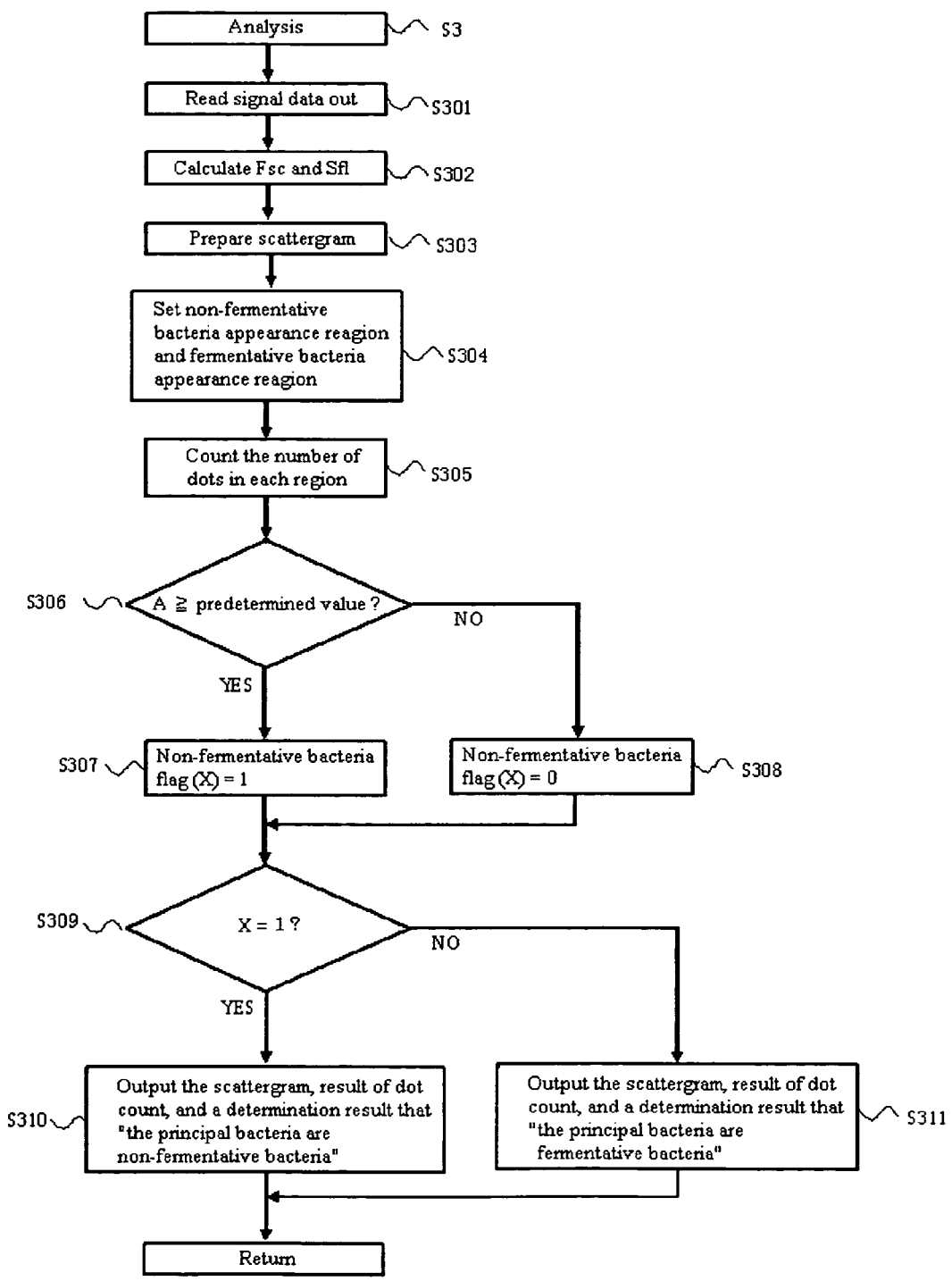
FIG. 7 is a view describing a flow of analysis in the bacteria analyzing apparatus according to one embodiment of the present invention.

When a forward scattered light signal and a side fluorescent light signal are detected by the measurement of S2, analyzing section 35 then analyzes each signal in accordance with the analyzing programs. An operation of the analyzing programs in S3 will be described with reference to the flowchart of FIG. 7. Each step in the flowchart is as follows.

S301: The data of the forward scattered light signal and the side fluorescent light signal detected from the sample liquid are read out from storage section 34. Then, the procedure goes to S302.

S302: The forward scattered light intensity (Fsc) and the side fluorescent light intensity (FL) are calculated on the basis of the forward scattered light signal and the side fluorescent light signal obtained from each particle in the sample liquid. Subsequently, the procedure goes to S303.

S303: A scattergram is prepared using the Fsc and the FL of each particle calculated in S302 as parameters. This is carried out as follows. First, two-dimensional coordinates are developed taking the Fsc and the FL as axes, and then the coordinate position corresponding to each particle in the analyte sample is determined on the basis of the Fsc and the FL calculated in S302. In this manner, a scattergram is prepared using the Fsc and the FL as parameters. Then, the procedure goes to S304.

Figure 8:
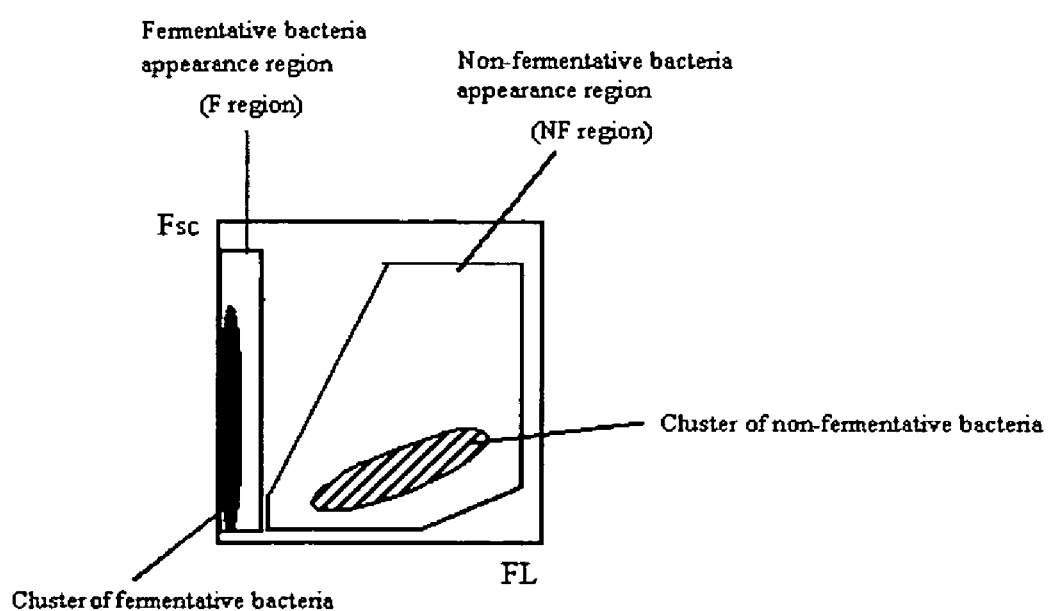
FIG. 8 is a model view illustrating one example of a two-dimensional scattergram prepared by the bacteria analyzing apparatus according to one embodiment of the present invention.

S304: A region where non-fermentative bacteria appear (this is referred to as NF region) and a region where fermentative bacteria appear (this is referred to as F region) are set on the prepared scattergram. The manner in which these regions are set on the scattergram is illustrated in FIG. 8. The NF region and the F region set here are empirically determined beforehand by measuring analyte samples containing the bacteria that are confirmed as non-fermentative bacteria and the bacteria that are confirmed as fermentative bacteria. This allows that, if the principal bacteria contained in a sample are non-fermentative bacteria, the dots corresponding to the non-fermentative bacteria in the sample form a cluster and appear in the NF region. On the other hand, if the principal bacteria contained in a sample are fermentative bacteria, the dots corresponding to the fermentative bacteria in the sample form a cluster and appear in the F region. Here, the data of coordinates in the NF region and the F region, which are stored in storage section 34, are read out by the analyzing programs in S304 and are applied onto the scattergram. Then, the procedure goes to S305.

S305: The number of dots in the NF region and in the F region is counted. Then, the procedure goes to S306.

S306: The number of dots appearing within the NF region and the number of dots appearing within the F region are compared, so as to determine which of the regions the cluster of dots appears in. First, assuming the number of dots appearing in the NF region to be NF and the number of dots appearing in the F region to be F, a value A is determined by the following calculation formula:

$$NF/(NF+F)=A$$

If the value of A calculated by the above formula is larger than or equal to a predetermined value (namely, if the colony of dots appears in the NF region), the procedure then goes to S307. On the other hand, if the value of A is smaller than the predetermined value (namely, if the colony of dots does not appear in the NF region), the procedure then goes to S308.

S307: The non-fermentative bacteria flag X is set to be "1". The procedure then goes to S309.

S308: The non-fermentative bacteria flag X is set to be "0". The procedure then goes to S309.

S309: In S309, a process of determining whether the non-fermentative bacteria flag X is "1" or not is executed. If the non-fermentative bacteria flag X is "1", the procedure goes to S310, whereas if the non-fermentative bacteria flag X is not "1", the procedure goes to S311.

S310: The scattergram prepared in S303 and S304, the count results of the number of dots in the NF region and in the F region counted in S305, and a message stating that "the principal bacteria contained in the specimen are non-fermentative bacteria" are displayed on liquid crystal touch panel 2.

S311: The scattergram prepared in S303 and S304, the count results of the number of dots in the NF region and in the F region counted in S305, and a message stating that "the principal bacteria contained in the specimen are fermentative bacteria" are displayed on liquid crystal touch panel 2.

The above is the flowchart of the measurement in this embodiment.

As described above, FIG. 8 is a view for describing the scattergram prepared in S303 and S304. In the scattergram, the axis of abscissa represents the FL, and the axis of ordinate represents the Fsc. In the axis of abscissa, the right side has a larger value of FL. In the axis of ordinate, the upper side has a larger value of Fsc. The non-fermentative bacteria appear within the NF region that is set on the scattergram. On the other hand, the fermentative bacteria appear within the F region that is set on the scattergram. Here, as described above, the non-fermentative bacteria have a higher degree of fluorescence stainability than the fermentative bacteria. Therefore, the fluorescence intensity detected from the non-fermentative bacteria is higher than the fluorescence intensity detected from the fermentative bacteria. For this reason, the NF region is set at a position corresponding to higher fluorescence intensity than the F region.

Hereafter, an example of the results of analyzing a specimen using bacteria analyzing apparatus 1 will be shown.

MEASUREMENT EXAMPLE 1

A specimen was prepared as follows. First, bacteria were cultivated in an agarose medium to form a colony of bacteria. Then, an intended kind of bacteria are collected from the colony, and are suspended into a heart infusion liquid medium so that the number of bacteria will have a concentration of about $10^5$/ml. In this example, bacteria liquid was prepared for each of the seven kinds of bacteria in all, and used as a specimen. Among the seven kinds of bacteria, the fermentative bacteria are four kinds including E. coli, K. pneumoniae, L. achidophilus, and S. aureus. The non-fermentative bacteria are three kinds including P. aeruginosa, A. baumannii, and E. faecalis. The scattergram obtained by analyzing the bacteria liquid of each of the bacteria prepared by the aforementioned method using bacteria analyzing apparatus 1 is shown in FIGS. 9 and 10.

Figure 9A:
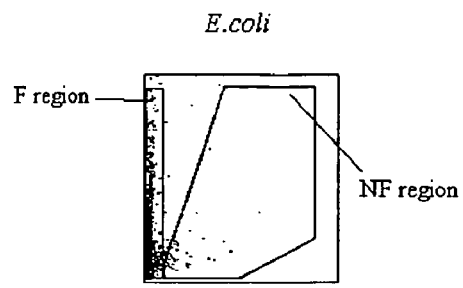
FIGS. 9A to 9D are views illustrating one example of two-dimensional scattergrams prepared by the bacteria analyzing apparatus according to one embodiment of the present invention.
Figure 9B:
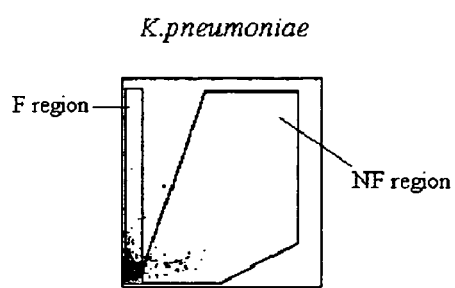
Figure 9C:
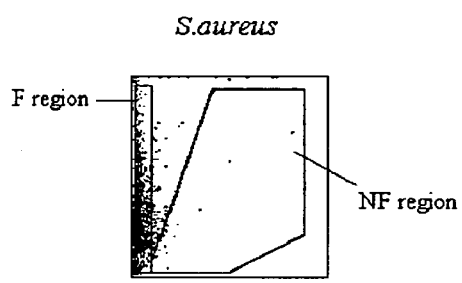
Figure 9D:
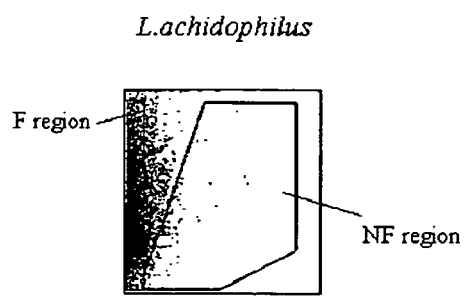

FIGS. 9A to 9D are scattergrams obtained using the bacteria liquid of the fermentative bacteria as a specimen. FIG. 9A shows a scattergram obtained by analyzing the bacteria liquid of E. coli. FIG. 9B shows a scattergram obtained by analyzing the bacteria liquid of K. pneumoniae. FIG. 9C shows a scattergram obtained by analyzing the bacteria liquid of S. aureus. FIG. 9D shows a scattergram obtained by analyzing the bacteria liquid of L. achidophilus. In all of FIGS. 9A, 9B, 9C and 9D, a cluster of dots is seen in the F region where fermentative bacteria appear.

Figure 10A:
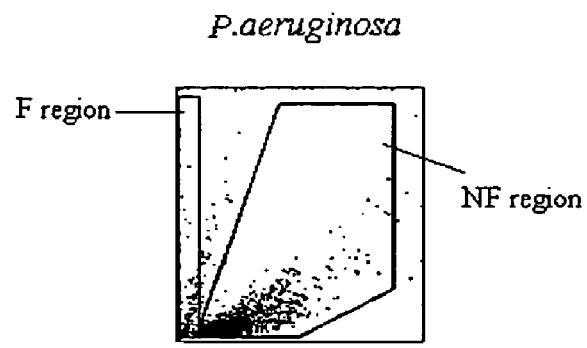
FIGS. 10A to 10C are views illustrating one example of two-dimensional scattergrams prepared by the bacteria analyzing apparatus according to one embodiment of the present invention.
Figure 10B:
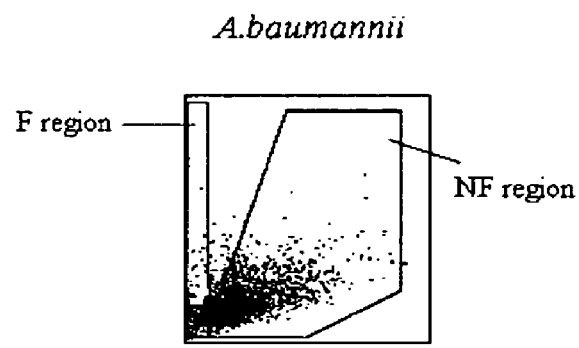
Figure 10C:
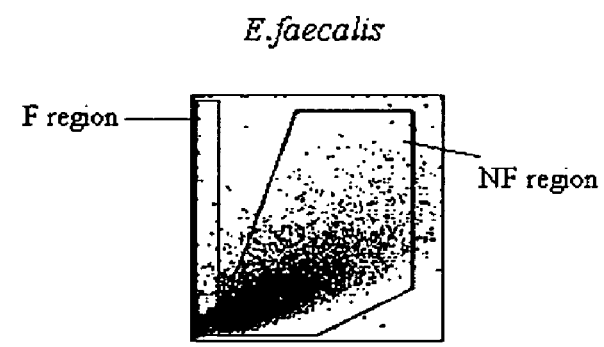

FIGS. 10A to 10C are scattergrams obtained using the bacteria liquid of the non-fermentative bacteria as a specimen. FIG. 10A shows a scattergram obtained by analyzing the bacteria liquid of P. aeruginosa. FIG. 10B shows a scattergram obtained by analyzing the bacteria liquid of A. baumannii. FIG. 10C shows a scattergram obtained by analyzing the bacteria liquid of E. faecalis. In all of FIGS. 10A, 10B and 10C, a cluster of dots is seen in the NF region where non-fermentative bacteria appear.

By FIGS. 9 and 10, it has been confirmed that the cluster of non-fermentative bacteria appears in the NF region where non-fermentative bacteria appear, and that the cluster of fermentative bacteria appears in the F region where fermentative bacteria appear. Thus, since the sites of appearance of fermentative bacteria and non-fermentative bacteria differ greatly on the scattergram, the fermentative bacteria can be easily distinguished from the non-fermentative bacteria.

The Methyl Red reaction test shown as a prior art in the above description requires cultivation for examining whether the bacteria decompose sugar or not in order to detect fermentative bacteria. For this reason, it requires two or three days before the fermentative bacteria are detected. In contrast, bacteria analyzing apparatus 1 eliminates the need for cultivation to examine whether the bacteria decompose sugar or not. Therefore, with the use of bacteria analyzing apparatus 1, the prepared bacteria liquid can be used as a specimen for measurement, and the results can be obtained at once.

Next, an example of the results obtained by analyzing urine collected from a patient as a specimen using bacteria analyzing apparatus 1 will be described below.

MEASUREMENT EXAMPLE 2

The specimens put to use were four specimens from A to D. Specimen A is urine of a human containing E. coli (fermentative bacteria); specimen B is urine of a human containing S. aureus (fermentative bacteria); specimen C is urine of a human containing E. faecalis (non-fermentative bacteria); and specimen D is urine of a human containing P. aeruginosa (non-fermentative bacteria).

Figure 11A:
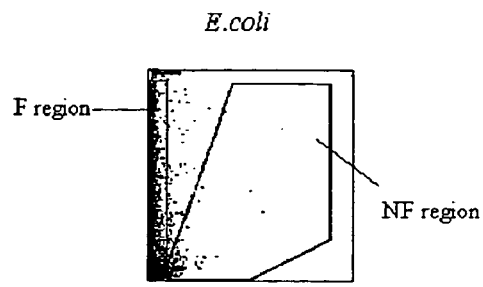
FIGS. 11A to 11D are views illustrating one example of two-dimensional scattergrams prepared by the bacteria analyzing apparatus according to one embodiment of the present invention.
Figure 11B:
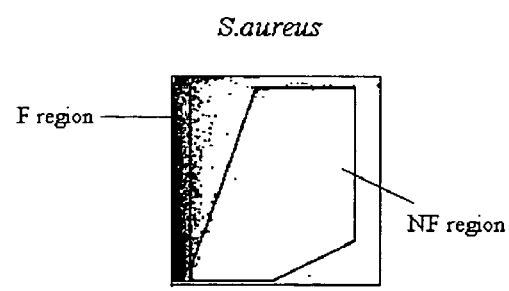
Figure 11C:
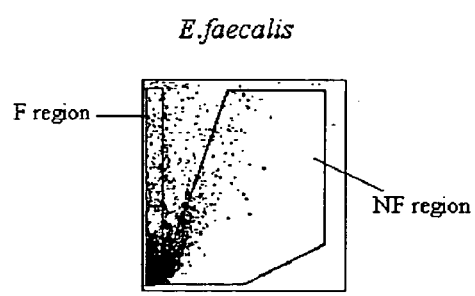
Figure 11D:
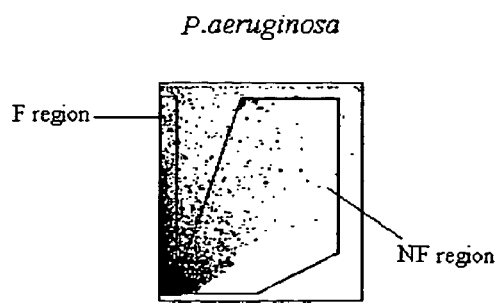

The scattergrams obtained by analyzing the above-described four specimens from A to D with the use of bacteria analyzing apparatus 1 are shown in FIGS. 11A to 11D. FIG. 11A shows a scattergram obtained by analyzing specimen A. FIG. 11B shows a scattergram obtained by analyzing specimen B. FIG. 11C shows a scattergram obtained by analyzing specimen C. FIG. 11D shows a scattergram obtained by analyzing specimen D. Regarding specimen A and specimen B, the cluster of dots appears in all cases in the F region where fermentative bacteria appear. On the other hand, regarding specimen C and specimen D, the cluster of dots appears in all cases in the NF region where non-fermentative bacteria appear.

The results of determination whether the principal bacteria contained in a specimen are fermentative bacteria or non-fermentative bacteria with the use of bacteria analyzing apparatus 1 on the basis of the appearance regions of the cluster of dots in a scattergram are shown in the following table.

TABLE 1

| Specimen | Determination result |
|---|---|
| A | Fermentative bacteria |
| B | Fermentative bacteria |
| C | Non-fermentative bacteria |
| D | Non-fermentative bacteria |

As shown in Table 1, the principal bacteria contained in the urine of specimen A and specimen B were determined to be fermentative bacteria, and the principal bacteria contained in the urine of specimen C and specimen D were determined to be non-fermentative bacteria. Also, in all of the cases of specimen A, specimen B, specimen C, and specimen D, the results of determination of the bacteria kind based on the analysis results coincide with the kinds of bacteria that are really contained in each specimen.

In the above-described embodiment, the fermentative bacteria and the non-fermentative bacteria contained in a specimen can be speedily detected to determine whether the principal bacteria contained in the specimen are fermentative bacteria or non-fermentative bacteria. The Methyl Red reaction test shown as a prior art in the above description requires cultivation for examining whether the bacteria decompose sugar or not, so that it requires two or three days before the fermentative bacteria are detected. In contrast, the present embodiment eliminates the need for cultivation to examine whether the bacteria decompose sugar or not, so that the prepared bacteria liquid can be used as a specimen for measurement, and the results can be obtained at once.

Further, in the above-described embodiment, the urine or blood collected from a patient can be used, as it is, as a specimen for measurement, without preparing a bacteria liquid such as described above. This allows that one can speedily determine whether the kind of the principal bacteria contained in a specimen is fermentative bacteria or non-fermentative bacteria.

Figure 12:
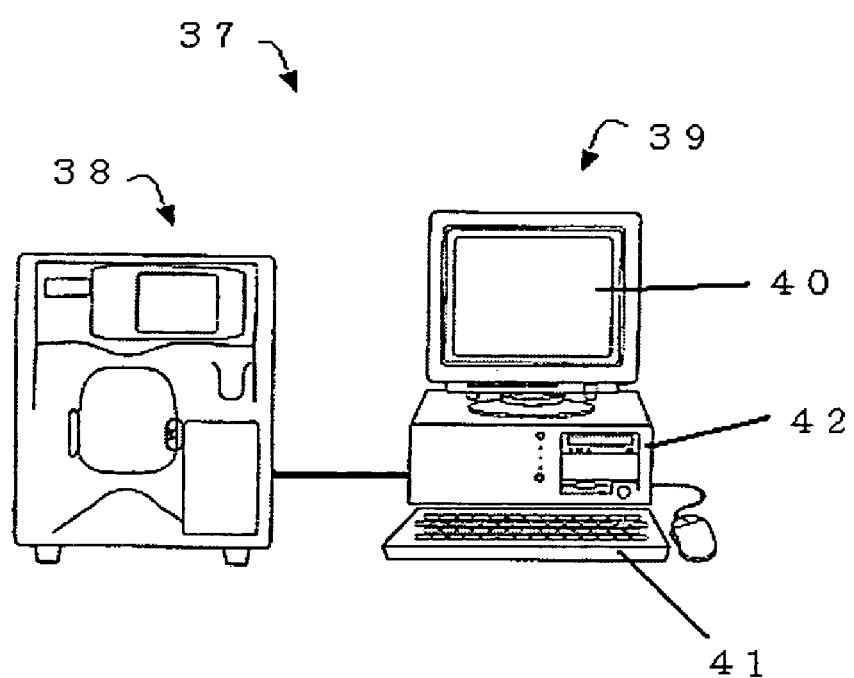
FIG. 12 is a view describing a construction of a bacteria analyzing apparatus according to another embodiment of the present invention.

Here, bacteria analyzing apparatus 1 of the above-described embodiment is an apparatus in which all the constituents are integrated; however, the present invention is not limited to this construction alone. For example, it may be an apparatus such as shown in FIG. 12 in which a part of the constituents are separately provided. A bacteria analyzing apparatus 37 of FIG. 12 is made of a measuring apparatus main body 38 and a personal computer 39. Further, though not illustrated in the drawings, measuring apparatus main body 38 has a start switch, an analyte sample preparing section for preparing a sample liquid, a measuring section for detecting signals from the sample liquid, and a first controlling section that controls the operation of the apparatus. The first controlling section has a first storage section that stores controlling programs for controlling the operation of each device and an operation controlling section for controlling the operation of each device in accordance with the controlling programs stored in the first storage section. Personal computer 39 has an output screen 40 for outputting and displaying the measurement results, an input section 41 for performing various setting inputs, and a second controlling section 42 that controls an analysis process. Second controlling section 42 has a second storage section for storing the analyzing programs and the results of processing by the analyzing programs, and an analyzing section for performing analysis on the basis of the data obtained by the measurement. Measuring apparatus main body 38 and personal computer 39 of FIG. 12 are connected via a connective device. The operation of each section in measurement apparatus main body 38 is controlled in accordance with the first controlling section of measuring apparatus main body 38. The measurement data obtained in measuring apparatus main body 38 are stored into the second storage section of personal computer 39 and analyzed by the analyzing section.

Further, in the analysis (S3) of bacteria analyzing apparatus 1 of the above-described embodiment, the region (F region) where the dots corresponding to fermentative bacteria appear and the region (NF region) where the dots corresponding to non-fermentative bacteria appear are both set on the scattergram; however, the present invention is not limited to this alone. For example, on the scattergram, one may set only the region (NF region) where the dots corresponding to non-fermentative bacteria appear. In this case, the non-fermentative bacteria contained in a specimen are detected by determining whether the dots appear in the NF region that is set on the scattergram.

Further, in the analysis (S3) of bacteria analyzing apparatus 1 of the above-described embodiment, whether the principal bacteria contained in a specimen are fermentative bacteria or non-fermentative bacteria is determined; however, the present invention is not limited to this alone. For example, in the case of analyzing a "specimen containing only one kind of bacteria" such as used in the measurement example 1, the bacteria of the specimen can be classified to either fermentative bacteria or non-fermentative bacteria, since it is clear that the bacteria contained in the specimen is only one kind. Therefore, in this case, whether the kind of bacteria contained in the specimen is fermentative bacteria or non-fermentative bacteria may be determined in the analysis (S3).

In addition, in the analysis (S3) of bacteria analyzing apparatus 1 of the above-described embodiment, the number of fermentative bacteria and the number of non-fermentative bacteria contained in a specimen may further be calculated. On the scattergram, the dots corresponding to fermentative bacteria appear in the F region and the dots corresponding to non-fermentative bacteria appear in the NF region. This allows that the number of fermentative bacteria and the number of non-fermentative bacteria contained in a specimen can be calculated on the basis of the number of dots appearing in the F region and the number of dots appearing in the NF region.

Further, in the case of performing measurement using a "specimen containing only one kind of bacteria", the number of bacteria may be calculated only for the bacteria that are determined in the analysis step. For example, if it is determined that the principal bacteria contained in a specimen are non-fermentative bacteria in the analysis step, the number of non-fermentative bacteria contained in the specimen is calculated on the basis of the number of dots appearing in the NF region, without calculating the number of fermentative bacteria. On the other hand, if it is determined that the principal bacteria contained in a specimen are fermentative bacteria in the analysis step, the number of fermentative bacteria contained in the specimen is calculated on the basis of the number of dots appearing in the F region, without calculating the number of non-fermentative bacteria.

Further, in the case of performing measurement using a "specimen containing bacteria and particles other than bacteria" such as urine, the particles other than bacteria (hereafter referred to as impurities) may be stained together with the bacteria, and the dots corresponding to the impurities may appear in the F region. Therefore, in calculating the number of fermentative bacteria contained in a specimen on the basis of the number of dots appearing in the F region, the correct number of fermentative bacteria may not be calculated due to the influence of the impurities. Thus, in performing measurement using a "specimen containing bacteria and impurities", the analysis step may calculate only the number of non-fermentative bacteria without calculating the number of fermentative bacteria. In this case, the number of non-fermentative bacteria contained in the specimen is calculated on the basis of the number of dots appearing in the NF region.

Further, even if a "specimen containing bacteria and impurities" is used for measurement, the number of fermentative bacteria can be determined on condition that the total number of bacteria contained in the specimen can be determined. In this case, in the analysis step, the number of non-fermentative bacteria contained in the specimen is calculated on the basis of the number of dots appearing in the NF region. Then, by subtracting the number of non-fermentative bacteria from the total number of bacteria determined in advance, the number of fermentative bacteria contained in the specimen is calculated. Here, the total number of bacteria contained in the specimen can be determined, for example, by using a method disclosed in European Patent Publication No. 1136563.

What is claimed is:

1. An apparatus for analyzing bacteria, comprising:
   an analyte sample preparing section configured for preparing an analyte sample by mixing an acidic solution with a specimen and staining bacteria in the resultant mixture with a reagent comprising a fluorescent dye;
   a scattered light detector configured for detecting scattered light from the bacteria;
   a fluorescent light detector configured for detecting fluorescent light from the bacteria;
   a storage section comprising a predetermined range of scattered light intensity and fluorescent light intensity indicative of non-fermentative bacteria;
   a light intensity obtainer configured for obtaining scattered light intensities of the bacteria based on the detected scattered light, and for obtaining fluorescent light intensities of the bacteria based on the detected fluorescent light; and
   a bacteria type determiner configured for determining non-fermentative bacterium when both the scattered light intensity and the fluorescent light intensity of the bacterium are within the predetermined range;
   wherein live fermentative bacteria in the specimen are differentiated from live non-fermentative bacteria in the specimen, wherein live fermentative bacteria decompose sugar to produce an acidic product, and wherein live non-fermentative bacteria are incapable of decomposing sugar.

2. The apparatus according to claim 1, wherein said analyte sample preparing section performs fluorescent staining on the specimen so as to generate a difference in fluorescence intensity between fermentative bacteria and non-fermentative bacteria.

3. The apparatus according to claim 1, wherein said analyte sample preparing section comprises a liquid mixing mechanism configured for mixing the acidic solution with the specimen.

4. The apparatus according to claim 1, wherein said analyte sample preparing section comprises a liquid mixing mechanism configured for mixing the acidic solution with the specimen, and for mixing the resultant mixture with the reagent comprising the fluorescent dye.

5. The apparatus according to claim 4, wherein the acidic solution is in the range of pH 1.0 to 3.0.

6. The apparatus according to claim 1, wherein a number of non-fermentative bacteria is calculated on the basis of both the scattered light intensity and the fluorescent light intensity of each bacterium.

7. The apparatus according to claim 1, wherein the analyte sample preparing section comprises a container comprising an acidic solution which is in the range of pH 1.0 to 3.0.

8. An apparatus for analyzing bacteria, comprising:
   an analyte sample preparing section configured for preparing an analyte sample by mixing an acidic solution with a specimen and staining bacteria in the resultant mixture with a reagent comprising a fluorescent dye;
   a scattered light detector configured for detecting scattered light from the bacteria;
   a fluorescent light detector configured for detecting fluorescent light from the bacteria;
   a storage section comprising a predetermined range of scattered light intensity and fluorescent light intensity indicative of fermentative bacteria, and a predetermined range of scattered light intensity and fluorescent light intensity indicative of non-fermentative bacteria;
   a light intensity obtainer configured for obtaining scattered light intensities of the bacteria based on the detected scattered light, and for obtaining fluorescent light intensities of the bacteria based on the detected fluorescent light; and
   a bacteria type determiner configured for determining fermentative bacterium when both the scattered light intensity and the fluorescent light intensity of the bacterium are within the predetermined range for determining fermentative bacteria, and for determining non-fermentative bacterium when both the scattered light intensity and the fluorescent light intensity of the bacterium are within the predetermined range for determining non-fermentative bacteria;
   wherein live fermentative bacteria in the specimen are differentiated from live non-fermentative bacteria in the specimen, wherein live fermentative bacteria decompose sugar to produce an acidic product, and wherein live non-fermentative bacteria are incapable of decomposing sugar.

9. The apparatus according to claim 8, wherein said analyte sample preparing section performs fluorescent staining on the specimen so as to generate a difference in fluorescence intensity between fermentative bacteria and non-fermentative bacteria.

10. The apparatus according to claim 8, wherein said analyte sample preparing section comprises a liquid mixing mechanism configured for mixing the acidic solution with the specimen.

11. The apparatus according to claim 8, wherein said analyte sample preparing section comprises a liquid mixing mechanism configured for mixing the acidic solution with the specimen, and for mixing the resultant mixture with the reagent comprising the fluorescent dye.

12. The apparatus according to claim 11, wherein the acidic solution is in the range of pH 1.0 to 3.0.

13. The apparatus according to claim 8, wherein a determination as to whether principal bacteria contained in the specimen are fermentative bacteria or non-fermentative bacteria is made on the basis of both the scattered light intensity and the fluorescent light intensity of each bacterium.

14. The apparatus according to claim 8, wherein fermentative bacteria and non-fermentative bacteria are detected on the basis of both the scattered light intensity and the fluorescent light intensity of each bacterium and a determination as to whether the kind of bacteria contained in the specimen is fermentative bacteria or non-fermentative bacteria is made on the basis of a result of detecting the fermentative bacteria and non-fermentative bacteria.

15. The apparatus according to claim 8, wherein fermentative bacteria and non-fermentative bacteria are detected on the basis of both the scattered light intensity and the fluorescent light intensity of each bacterium, and a determination as to whether principal bacteria contained in the specimen are fermentative bacteria or non-fermentative bacteria is made on the basis of a result of detecting the fermentative bacteria end non-fermentative bacteria.

16. The apparatus according to claim 8, wherein the analyte sample preparing section comprises a container comprising an acidic solution which is in the range of pH 1.0 to 3.0.

* * * * *

UNITED STATES PATENT AND TRADEMARK OFFICE
CERTIFICATE OF CORRECTION

PATENT NO.      : 7,582,473 B2                                                                 Page 1 of 1
APPLICATION NO. : 10/922522
DATED           : September 1, 2009
INVENTOR(S)     : Yasuyuki Kawashima It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 461 days.

Signed and Sealed this

Fourteenth Day of September, 2010

David J. Kappos
*Director of the United States Patent and Trademark Office*